(12) United States Patent
Hurt (10) Patent No.: US 9,694,166 B2
(45) Date of Patent: Jul. 4, 2017

(54) METHOD OF DRAINING CEREBROSPINAL FLUID

(75) Inventor: Robert F. Hurt, Boulder Junction, WI (US)

(73) Assignee: Medtronics PS Medical, Inc., Goleta, CA (US)

( * ) Notice: Subject to any disclaimer, the term of this patent is extended or adjusted under 35 U.S.C. 154(b) by 801 days.

(21) Appl. No.: 13/022,809

(22) Filed: Feb. 8, 2011

(65) Prior Publication Data

US 2011/0282264 A1 Nov. 17, 2011

Related U.S. Application Data

(60) Continuation-in-part of application No. 11/546,886, filed on Oct. 12, 2006, now abandoned, which is a division of application No. 10/400,363, filed on Mar. 26, 2003, now abandoned.

(60) Provisional application No. 60/367,565, filed on Mar. 26, 2002.

(51) Int. Cl.
*A61M 27/00* (2006.01)
*A61M 25/00* (2006.01)

(52) U.S. Cl.
CPC ........ *A61M 27/006* (2013.01); *A61M 25/007* (2013.01); *A61M 2025/0073* (2013.01)

(58) Field of Classification Search
USPC ......................................... 604/8, 9, 265, 540
See application file for complete search history.

(56) References Cited

U.S. PATENT DOCUMENTS

| 105,210 A | 7/1870 | Horton |
| 2,182,567 A | 12/1939 | Mantell |
| 3,089,031 A | 5/1963 | Endter |

(Continued)

FOREIGN PATENT DOCUMENTS

| EP | 0381062 A2 | 1/1990 |
| GB | 2108393 | 5/1983 |

(Continued)

OTHER PUBLICATIONS http://www/ncbi.nlm.nih.gov/pubmed/15368131.
(Continued)

*Primary Examiner* — Tatyana Zalukaeva
*Assistant Examiner* — Benjamin Klein
(74) *Attorney, Agent, or Firm* — Dicke, Billig & Czaja, PLLC (57) ABSTRACT

A method of draining cerebrospinal fluid from a human brain. The method includes providing a drainage catheter having a proximal end and a distal end. The drainage catheter has a plurality of openings formed therein. The plurality of openings includes a first opening, a second opening, and a most proximal opening. The second opening is disposed closer to the distal end than the first opening. A cross-sectional area of the first opening is less than a cross-sectional area of the second opening. The distal end of the drainage catheter is inserted into a human brain. Cerebrospinal fluid is drained from the human brain. The cerebrospinal fluid passes into the drainage catheter through the plurality of openings and out of the drainage catheter through the proximal end. A rate at which the cerebrospinal fluid passes through the drainage catheter is controlled to maintain intracranial pressure within a selected range.

14 Claims, 5 Drawing Sheets

(56) References Cited

U.S. PATENT DOCUMENTS

| | | |
|---|---|---|
| 3,241,554 A | 3/1966 | Coanda |
| 3,421,510 A | 1/1969 | Kettenbach |
| 3,516,410 A | 6/1970 | Hakim |
| 3,626,950 A | 12/1971 | Schulte |
| 3,690,323 A | 9/1972 | Wortman et al. |
| 3,810,471 A | 5/1974 | Truhan |
| 3,828,774 A | 8/1974 | Vass |
| 3,889,687 A | 6/1975 | Harris et al. |
| 3,924,635 A | 12/1975 | Hakim |
| RE28,686 E | 1/1976 | Coulthard |
| 3,965,901 A | 6/1976 | Penny et al. |
| 3,985,140 A | 10/1976 | Harris |
| 3,991,768 A | 11/1976 | Portnoy |
| 4,026,276 A | 5/1977 | Chubbuck |
| 4,156,422 A | 5/1979 | Hildebrandt et al. |
| 4,211,325 A | 7/1980 | Wright |
| 4,215,695 A | 8/1980 | Spitz et al. |
| 4,255,968 A | 3/1981 | Harpster |
| 4,281,667 A | 8/1981 | Cosman |
| 4,332,255 A | 6/1982 | Hakim et al. |
| 4,354,506 A | 10/1982 | Sakaguchi et al. |
| 4,377,169 A | 3/1983 | Banks |
| 4,382,445 A | 5/1983 | Sommers |
| 4,387,715 A | 6/1983 | Hakim et al. |
| 4,443,214 A | 4/1984 | Marion |
| 4,451,252 A | 5/1984 | Martin |
| 4,464,168 A | 8/1984 | Redmond et al. |
| 4,519,401 A | 5/1985 | Ko et al. |
| 4,540,400 A | 9/1985 | Hooven |
| 4,548,516 A | 10/1985 | Helenowski |
| 4,551,128 A | 11/1985 | Hakim et al. |
| 4,560,375 A | 12/1985 | Schulte et al. |
| 4,576,182 A | 3/1986 | Normann |
| 4,595,390 A | 6/1986 | Hakim et al. |
| 4,605,395 A | 8/1986 | Rose et al. |
| 4,615,691 A | 10/1986 | Hakim et al. |
| 4,621,654 A | 11/1986 | Holter |
| 4,627,443 A | 12/1986 | Chubbuck et al. |
| 4,636,194 A | 1/1987 | Schulte et al. |
| 4,655,745 A | 4/1987 | Corbett |
| 4,660,568 A | 4/1987 | Cosman |
| 1,676,772 A | 6/1987 | Hooven |
| 4,673,384 A | 6/1987 | Marion |
| 4,676,772 A | 6/1987 | Hooven |
| 4,681,559 A | 7/1987 | Hooven |
| 4,705,499 A | 11/1987 | Hooven |
| 4,741,730 A | 5/1988 | Dormandy, Jr. et al. |
| 4,767,400 A | 8/1988 | Miller et al. |
| 4,769,002 A | 9/1988 | Hooven |
| 4,772,257 A | 9/1988 | Hakim et al. |
| 4,776,838 A | 10/1988 | Sainte-Rose et al. |
| 4,781,673 A | 11/1988 | Watanabe |
| 4,781,674 A | 11/1988 | Redmond et al. |
| 4,787,886 A | 11/1988 | Cosman |
| 4,861,331 A | 8/1989 | East et al. |
| 4,865,600 A | 9/1989 | Carpentier et al. |
| 4,867,740 A | 9/1989 | East |
| 4,867,741 A | 9/1989 | Portnoy |
| 4,885,002 A | 12/1989 | Watanabe et al. |
| 4,904,236 A | 2/1990 | Redmond et al. |
| 4,950,232 A | 8/1990 | Ruzicka et al. |
| 5,042,974 A | 8/1991 | Agarwal |
| 5,054,518 A | 10/1991 | Rancani |
| 5,066,278 A | 11/1991 | Hirschberg et al. |
| 5,069,663 A | 12/1991 | Sussman |
| 5,117,836 A | 6/1992 | Millar |
| 5,154,693 A | 10/1992 | East et al. |
| 5,167,615 A | 12/1992 | East et al. |
| 5,180,387 A | 1/1993 | Ghajar et al. |
| 5,191,898 A | 3/1993 | Millar |
| 5,207,661 A | 5/1993 | Repschlager |
| 5,291,899 A | 3/1994 | Watanabe et al. |
| 5,304,114 A | 4/1994 | Cosman et al. |
| 5,336,166 A | 8/1994 | Sierra |
| 5,352,207 A | 10/1994 | Nussbaum |
| 5,368,556 A | 11/1994 | Lecuyer |
| 5,368,704 A | 11/1994 | Madou et al. |
| 5,385,541 A * | 1/1995 | Kirsch et al. ................ 604/8 |
| 5,387,188 A | 2/1995 | Watson |
| 5,405,316 A | 4/1995 | Magram |
| 5,425,723 A | 6/1995 | Wang |
| 5,437,626 A | 8/1995 | Cohen et al. |
| 5,437,627 A | 8/1995 | Lecuyer |
| 5,443,502 A | 8/1995 | Caudillo et al. |
| 5,451,215 A | 9/1995 | Wolter |
| 5,458,606 A | 10/1995 | Cohen et al. |
| 5,476,510 A | 12/1995 | Eberhardt et al. |
| 5,480,425 A | 1/1996 | Ogilive |
| 5,507,795 A | 4/1996 | Chiang et al. |
| 5,520,662 A | 5/1996 | Moss |
| 5,531,673 A | 7/1996 | Helenowski |
| 5,549,665 A | 8/1996 | Vesely et al. |
| 5,598,847 A | 2/1997 | Renger |
| 5,637,083 A | 6/1997 | Bertrand et al. |
| 5,643,195 A | 7/1997 | Drevet et al. |
| 5,662,600 A | 9/1997 | Watson et al. |
| 5,662,704 A | 9/1997 | Gross |
| 5,683,357 A | 11/1997 | Magram |
| 5,704,352 A | 1/1998 | Tremblay et al. |
| 5,716,401 A | 2/1998 | Eberhardt et al. |
| 5,728,061 A | 3/1998 | Ahmed |
| 5,730,720 A | 3/1998 | Sites et al. |
| 5,776,187 A | 7/1998 | Krueger et al. |
| 5,782,811 A | 7/1998 | Samson et al. |
| 5,800,376 A | 9/1998 | Watson et al. |
| 5,800,407 A | 9/1998 | Eldor |
| 5,810,760 A | 9/1998 | Andrews |
| 5,810,761 A | 9/1998 | Saens-Arrollo |
| 5,843,013 A | 12/1998 | Lecuyer et al. |
| 5,928,181 A | 7/1999 | Coleman et al. |
| 5,928,182 A | 7/1999 | Kraus et al. |
| 5,931,831 A | 8/1999 | Linder |
| 5,935,084 A | 8/1999 | Southworth |
| 5,957,853 A | 9/1999 | Giuffre |
| 5,968,004 A | 10/1999 | Gorsuch |
| 5,980,480 A | 11/1999 | Rubenstein et al. |
| 6,007,510 A | 12/1999 | Nigam |
| 6,050,969 A | 4/2000 | Kraus |
| 6,090,062 A | 7/2000 | Sood et al. |
| 6,096,019 A | 8/2000 | Andrews |
| 6,110,139 A | 8/2000 | Loubser |
| 6,113,553 A | 9/2000 | Chubbuck |
| 6,117,125 A | 9/2000 | Rothbarth et al. |
| 6,126,007 A | 10/2000 | Kari et al. |
| 6,126,628 A | 10/2000 | Nissels |
| 6,132,405 A | 10/2000 | Nilsson et al. |
| 6,135,992 A | 10/2000 | Wang |
| 6,193,682 B1 | 2/2001 | Ahmed |
| 6,193,691 B1 | 2/2001 | Beardsley |
| 6,206,885 B1 | 3/2001 | Ghahremani et al. |
| 6,241,660 B1 | 6/2001 | Dolle |
| 6,248,080 B1 | 6/2001 | Miesel et al. |
| 6,264,625 B1 | 7/2001 | Rubenstein et al. |
| 6,283,934 B1 | 9/2001 | Borgesen |
| 6,296,633 B1 | 10/2001 | Helgerson |
| 6,338,727 B1 | 1/2002 | Noda et al. |
| 6,338,740 B1 | 1/2002 | Carpentier |
| 6,342,120 B1 | 1/2002 | Basta |
| 6,350,253 B1 | 2/2002 | Deniega et al. |
| 6,371,464 B1 | 4/2002 | Porche et al. |
| 6,383,159 B1 | 5/2002 | Saul et al. |
| 6,383,160 B1 | 5/2002 | Madsen |
| 6,391,019 B1 | 5/2002 | Ito |
| 6,409,758 B2 | 6/2002 | Stobie et al. |
| 6,413,233 B1 | 7/2002 | Sites et al. |
| 6,432,050 B1 | 8/2002 | Porat et al. |
| 6,433,050 B1 | 8/2002 | Shinomiya et al. |
| 6,439,538 B1 | 8/2002 | Ito |
| 6,453,185 B1 | 9/2002 | O'Keefe |
| 6,485,449 B2 | 11/2002 | Ito |
| 6,524,268 B2 | 2/2003 | Hayner et al. |
| 6,524,300 B2 | 2/2003 | Meglin |
| 6,533,733 B1 | 3/2003 | Ericson et al. |
| 6,544,208 B2 | 4/2003 | Ethier et al. |

(56) References Cited

U.S. PATENT DOCUMENTS

| | | |
|---|---|---|
| 6,547,724 B1 | 4/2003 | Soble et al. |
| 6,558,418 B2 | 5/2003 | Carpentier et al. |
| 6,575,928 B2 | 6/2003 | Saul et al. |
| 6,585,677 B2 | 7/2003 | Cowan, Jr. et al. |
| 6,589,189 B2 | 7/2003 | Meyerson et al. |
| 6,600,945 B2 | 7/2003 | Ginggen et al. |
| 6,626,838 B2 | 9/2003 | Doten et al. |
| 6,626,885 B2 | 9/2003 | Massengale |
| 6,645,244 B2 | 11/2003 | Shu et al. |
| 6,663,353 B2 | 12/2003 | Lipscomb et al. |
| 6,673,022 B1 | 1/2004 | Bobo et al. |
| 6,682,508 B1 | 1/2004 | Meythaler et al. |
| 6,685,638 B1 | 2/2004 | Taylor et al. |
| 6,689,085 B1 | 2/2004 | Rubenstein et al. |
| 6,692,514 B2 | 2/2004 | Fogarty et al. |
| 6,695,147 B1 | 2/2004 | Yager et al. |
| 6,702,249 B2 | 3/2004 | Ito |
| 6,702,852 B2 | 3/2004 | Stobie et al. |
| 6,731,976 B2 | 5/2004 | Penn et al. |
| 6,736,845 B2 | 5/2004 | Marquez et al. |
| 6,749,574 B2 | 6/2004 | O'Keefe |
| 6,758,828 B2 | 7/2004 | Hammer et al. |
| 6,758,832 B2 | 7/2004 | Barbut et al. |
| 6,761,718 B2 | 7/2004 | Madsen |
| 6,802,811 B1 | 10/2004 | Slepian |
| 6,813,944 B2 | 11/2004 | Mayer et al. |
| 6,840,917 B2 | 1/2005 | Marion |
| 6,851,453 B2 | 2/2005 | Lipscomb et al. |
| 6,875,192 B1 | 4/2005 | Saul et al. |
| 6,881,197 B1 | 4/2005 | Nigam |
| 6,881,210 B2 | 4/2005 | Wilson |
| 6,893,459 B1 | 5/2005 | Macoviak |
| 6,905,474 B2 | 6/2005 | Borgesen |
| 6,913,589 B2 | 7/2005 | Dextradeur et al. |
| 6,914,555 B2 | 7/2005 | Lipscomb et al. |
| 6,926,691 B2 | 8/2005 | Miethke |
| 6,932,787 B2 | 8/2005 | Cowan et al. |
| 6,953,444 B2 | 10/2005 | Rosenberg |
| 6,964,682 B2 | 11/2005 | Nguyen-Thien-Nhon et al. |
| 6,966,925 B2 | 11/2005 | Stobie |
| 7,004,923 B2 | 2/2006 | Deniega et al. |
| 7,011,647 B2 | 3/2006 | Purdy et al. |
| 7,014,624 B2 | 3/2006 | Meythaler et al. |
| 7,020,505 B1 | 3/2006 | Phillips et al. |
| 7,025,739 B2 | 4/2006 | Saul |
| 7,025,742 B2 | 4/2006 | Rubenstein et al. |
| 7,036,369 B2 | 5/2006 | Keppner et al. |
| 7,037,288 B2 | 5/2006 | Rosenberg et al. |
| 7,066,901 B2 | 6/2006 | Kuth et al. |
| 7,069,779 B2 | 7/2006 | Zumkehr et al. |
| 7,094,214 B2 | 8/2006 | Dextradeur et al. |
| 7,104,958 B2 | 9/2006 | Crutchfield et al. |
| 7,118,548 B2 | 10/2006 | Borgesen |
| 7,118,549 B2 | 10/2006 | Chan |
| 7,172,571 B2 | 2/2007 | Moskowitz et al. |
| 7,181,963 B2 | 2/2007 | Bork |
| 7,189,221 B2 | 3/2007 | Silverberg et al. |
| 7,195,608 B2 | 3/2007 | Burnett |
| 7,976,517 B2 * | 7/2011 | Dextradeur et al. ......... 604/265 |
| 8,123,714 B2 * | 2/2012 | Ludin et al. ............... 604/9 |
| 2001/0022350 A1 | 9/2001 | Ito |
| 2001/0034476 A1 | 10/2001 | Dolle |
| 2002/0004495 A1 | 1/2002 | Harada et al. |
| 2002/0022793 A1 | 2/2002 | Bertrand et al. |
| 2002/0026138 A1 | 2/2002 | Cowan, Jr. et al. |
| 2002/0045847 A1 | 4/2002 | Borgesen |
| 2002/0058901 A1 | 5/2002 | Marion |
| 2002/0065508 A1 | 5/2002 | Borgesen |
| 2002/0082547 A1 * | 6/2002 | Deniega et al. ............. 604/48 |
| 2002/0082686 A1 | 6/2002 | Nguyen-Thien-Nhon et al. |
| 2002/0087059 A1 | 7/2002 | O'Keefe |
| 2002/0087111 A1 | 7/2002 | Ethier et al. |
| 2002/0111601 A1 | 8/2002 | Thompson |
| 2002/0123713 A1 | 9/2002 | Watson |
| 2002/0123714 A1 | 9/2002 | Saul et al. |
| 2002/0128588 A1 | 9/2002 | Borgesen |
| 2002/0133142 A1 | 9/2002 | Deniega et al. |
| 2002/0133226 A1 | 9/2002 | Marquez et al. |
| 2002/0151770 A1 | 10/2002 | Noll, III et al. |
| 2002/0188246 A1 | 12/2002 | Hayner et al. |
| 2003/0009132 A1 | 1/2003 | Schwartz et al. |
| 2003/0032915 A1 | 2/2003 | Saul |
| 2003/0125805 A1 | 7/2003 | Johnson et al. |
| 2003/0135147 A1 | 7/2003 | Rosenberg et al. |
| 2003/0163079 A1 | 8/2003 | Burnett |
| 2003/0181864 A1 | 9/2003 | Deniega et al. |
| 2003/0216666 A1 | 11/2003 | Ericson et al. |
| 2003/0216710 A1 | 11/2003 | Hurt |
| 2003/0221524 A1 | 12/2003 | Hu |
| 2004/0010219 A1 | 1/2004 | McCusker et al. |
| 2004/0024451 A1 | 2/2004 | Johnson et al. |
| 2004/0030278 A1 | 2/2004 | Cowan, Jr. et al. |
| 2004/0030279 A1 | 2/2004 | Rubenstein et al. |
| 2004/0068201 A1 | 4/2004 | Saul |
| 2004/0068221 A1 | 4/2004 | Silverberg et al. |
| 2004/0073154 A1 | 4/2004 | Borgesen |
| 2004/0073194 A1 | 4/2004 | Olsen et al. |
| 2004/0082900 A1 | 4/2004 | Luttich |
| 2004/0092908 A1 | 5/2004 | Harper et al. |
| 2004/0092909 A1 | 5/2004 | Harper et al. |
| 2004/0092910 A1 | 5/2004 | Harper et al. |
| 2004/0122348 A1 | 6/2004 | Hokanson et al. |
| 2004/0138741 A1 | 7/2004 | Stobie et al. |
| 2004/0147871 A1 | 7/2004 | Burnett |
| 2004/0148018 A1 | 7/2004 | Carpentier et al. |
| 2004/0193094 A1 | 9/2004 | Kraus |
| 2004/0211416 A1 | 10/2004 | Lurie |
| 2004/0220510 A1 | 11/2004 | Koullick et al. |
| 2004/0243145 A1 | 12/2004 | Bobo, Sr. et al. |
| 2004/0260229 A1 | 12/2004 | Meir |
| 2004/0267187 A1 | 12/2004 | Rosenberg |
| 2005/0004460 A1 | 1/2005 | Taylor et al. |
| 2005/0010138 A1 | 1/2005 | Mangiardi et al. |
| 2005/0010159 A1 | 1/2005 | Reich et al. |
| 2005/0020962 A1 | 1/2005 | Reich et al. |
| 2005/0038371 A1 | 2/2005 | Reich et al. |
| 2005/0043669 A1 | 2/2005 | Rosenberg |
| 2005/0043670 A1 | 2/2005 | Rosenberg |
| 2005/0055009 A1 | 3/2005 | Rosenberg |
| 2005/0085763 A1 | 4/2005 | Ginggen et al. |
| 2005/0085764 A1 | 4/2005 | Borgesen |
| 2005/0090775 A1 | 4/2005 | Harper et al. |
| 2005/0092335 A1 | 5/2005 | Bertrand et al. |
| 2005/0096579 A1 | 5/2005 | Bertrand et al. |
| 2005/0096581 A1 | 5/2005 | Chan |
| 2005/0096582 A1 | 5/2005 | Burnett |
| 2005/0119602 A1 | 6/2005 | Murphy et al. |
| 2005/0171452 A1 | 8/2005 | Neff |
| 2005/0187488 A1 | 8/2005 | Wolf |
| 2005/0187509 A1 | 8/2005 | Wolf |
| 2005/0204811 A1 | 9/2005 | Neff |
| 2005/0256510 A1 | 11/2005 | Moskowitz et al. |
| 2005/0273034 A1 | 12/2005 | Burnett |
| 2005/0277865 A1 | 12/2005 | Gharib et al. |
| 2006/0000270 A1 | 1/2006 | Zumkehr et al. |
| 2006/0000271 A1 | 1/2006 | Bork |
| 2006/0000272 A1 | 1/2006 | Neuenschwander et al. |
| 2006/0000273 A1 | 1/2006 | Keppner et al. |
| 2006/0004317 A1 | 1/2006 | Mauge et al. |
| 2006/0020224 A1 | 1/2006 | Geiger |
| 2006/0036208 A1 | 2/2006 | Burnett |
| 2006/0047201 A1 | 3/2006 | Eide |
| 2006/0052737 A1 | 3/2006 | Bertrand et al. |
| 2006/0074371 A1 | 4/2006 | McCusker et al. |
| 2006/0074388 A1 | 4/2006 | Dextradeur et al. |
| 2006/0089589 A1 | 4/2006 | Portnoy |
| 2006/0111659 A1 | 5/2006 | Tyler |
| 2006/0149161 A1 | 7/2006 | Wilson |
| 2006/0184098 A1 | 8/2006 | Barnitz et al. |
| 2006/0210548 A1 | 9/2006 | Meythaler et al. |
| 2006/0211944 A1 | 9/2006 | Mauge et al. |
| 2006/0211945 A1 | 9/2006 | Mauge et al. |
| 2006/0211946 A1 | 9/2006 | Mauge et al. |
| 2006/0224101 A1 | 10/2006 | Glenn |

(56) References Cited

U.S. PATENT DOCUMENTS

| | | |
|---|---|---|
| 2006/0224102 A1 | 10/2006 | Glenn |
| 2006/0241545 A1 | 10/2006 | Madsen et al. |
| 2006/0247569 A1 | 11/2006 | Bertrand et al. |
| 2006/0258970 A1 | 11/2006 | Moskowitz et al. |
| 2006/0264799 A1 | 11/2006 | Caluori |
| 2006/0276743 A1 | 12/2006 | MacMahon et al. |
| 2007/0005000 A1 | 1/2007 | Ludin |
| 2007/0038171 A1 | 2/2007 | Mayer |
| 2007/0055196 A1 | 3/2007 | Gormley |

FOREIGN PATENT DOCUMENTS

| | | |
|---|---|---|
| GB | 2182567 | 5/1987 |
| GB | 2011259 | 1/2012 |
| WO | 9713543 A1 | 4/1997 |
| WO | 0105210 A2 | 1/2001 |
| WO | 0108573 A2 | 2/2001 |
| WO | 03089031 A1 | 10/2003 |

OTHER PUBLICATIONS http://www/ncbi.nlm.nih.gov/pubmed/964058.
http://www.clinicalservicesjournal.com/Story.aspx?Story=727.
http://www.diagnosticum.hu/hun/data/kheszkozok/pdf/02.pdf.
The Caroline Guide: A non-invasive Medical Device for the Placement of Shunts to Treat Hydrocephalus; Tech ID: 04-92-43; Jul. 10, 2001; 2 pages.
Radionics TeleSensor; May 4, 2000; 6 pages.
Hydrocephalus Ventricular Anatomy; May 27, 2000; 4 pages.
Morris, Martin J. PhD, Bradley University; Lin, Julian MD, University of Illinois College of Medicine at Peoria; "Multidisciplinary Approach to the Study of Proximal Ventricular Catheters," Nov. 2, 2001; Children's Hospital of Illinois; 25 pgs.
"Hydrocephalus," (retrieved on Jul. 10, 2002). Retrieved from the Internet: http://www.health.adalaide.edu.au/paedneuro/hydro.html; pp. 1-10.
"The Biomaterials—Related Infection Group," (retrieved on Sep. 9, 2011). Retrieved from the Internet: http://www.nottingham.ac.uk; pp. 1-3.
Sainte-Rose, Christian, M.D.; Hooven, Michael D., M.S.ME; Hirsch, Jean-Francois, M.D.; "A New Approach in the Treatment of Hydrocephalus," Neurosurgical Service, Hospital Necker-Enfants, Malades, Paris, France; J. Neurosurg. 66:213-216, vol. 66, Feb. 1987.
"Phoenix Anti-Block Catheter-Reservior," (retrieved May 7, 2000). Retrieved from the Internet: http://www.shunt.com/biomedical/instructions.NS.AntiBlockCR.html; 5 pages.
Collins, Patricia, Ph.D., S.R.N.; Hockley, Anthony D., F.R.C.S. (ED.); Woollam, David H.M., M.D., S.C.D., F.R.C.P., "Surface Ultrastructure of Tissues Occluding Ventricular Catheters," J. Neurosurg 48:609-613, vol. 48, Apr. 1978.
Sainte-Rose, C.; Pialt, J.H.; Renier, D.; Pierre-Kahm; Hirsch, J.F.; Hoffman, H.J.; Humphreys, R.P.; Hendrick, E.G.; "Mechanical Complications in Shunts," Pediatr Neurosurg 1991-92; 17:2-9.
Lin, Julian, M.D.; Morris, Martin, PhD.; Hurt, Robert PhD.; Olivero, William, M.D.; "A Computational and Experimental Study of Proximal Ventricular Catheters," 718 at Scientific Session II; Apr. 8, 2002; Dept. of Neurosurgery, University of Illinois College of Medicine; Dept. of Mechanical Engineering, Bradely University, Peoria, IL; 13 pgs.
"F647-94 Standard Practice for Evaluating and Specifying Implantable Shunt Assemblies for Neurosurgical Application," (retrieved on Jun. 22, 2000). Retrieved from the Internet: http://www.astm.org/cgi-bin/SoftCart.exe/Database.cart/pages/F647.html+nystore+kemi0257; pp. 146-156.
Sainte-Rose, C.; Hospital Necker-Enfants Malades, Service de Neurochimie, Paris, France; "Shunt Obstruction: A Preventable Complication'?" Complication Review; Pediatr Neurosurg 1993; 19:156-164.
Keyhani, Keyvan; Banerjee, Rupak; Hajiloo, Shoreh; Biomedical Applications Team and Consulting Services, Fluent Incorporated, Evanston, Illinois, Journal Articles by Fluent Software Users, JA102. "Computational Fluid Dynamics Streamlines Design and Manufacture of Medical Devices," pp. 1-4.
Oi, Shizuo, M.D.; Shimoda, Masami, M.D.; Shibata, Masayoshi, M.D.; Honda, Yumie, M.D.; Togo, Kouji, M.D.; Shinoda, Masaki, M.D.; Tsugane, Ryuichi, M.D.; Sato, Osamu, M.D.; "Pathophysiology of Long-Standing Overt Ventriculomegaly in Adults," Dept. of Neurosurg, 92:933-940, vol. 92, Jun. 2000.
Portnoy, Harold D., M.D.; Depart of Surgery (Neurosurger), Pontiac General Hospital, Pontiac Michigan; "New Ventricular Catheter for Hydrocephalic Shunts," J. Neurosurg, vol. 34, May 1971, pp. 702-703.
Couldwell, William T., M.D.; Ph.D.; Lemay, Daniel R., M.D., Ph.D.; Mccomn, Gordon J., M.D.; "Experience With Use of Extended Length Peritoneal Shunt Catheters;" The Division of Neurological Surgery, Childrens Hospital of Los Angeles, University of Southern California School of Medicine, Los Angeles, California; J. Neurosurg, vol. 85, Sep. 1996, pp. 425-427.
Rekate, Harold L; Brodkey, Jason A.; Chizeck, Howard J.: ElSakka W.; Ko Wen H.; "Ventricular Volume Regulation: A Mathematical Model and Computer Simulation," Section of Pediatric Neurosurgery, Barrow Neurological Institute, Phoenix, Ariz., USA; Cleveland, Ohio, USA; Pediatr Neurosci 1988; 14:77-84.
"Phoenix Anti-Block Ventricular Catheter," Retrieved from the Internet: http://www.shint.com/bimoedcal.instructions.NS.AntiBlokVC.html; 4 pages.
"Phoenix Neurosurgical Surgery Price List, Catheters and Reservoirs," Retrieved from the Internet: http://net-ez.com/biomedical/cr1.html; 2 pages.
Lin et al., "Computational and Experimental Study of Proximal Flow in Ventricular Catheters", J. Neurosurgery, vol. 99, Aug. 2003, (pp. 426-431).
Ginsberg, Howard J.; Sum, Alfred; Drake, James M.; Cobbold, Richard S.C.; Division of Neurosurgery; Hospital for Sick Children, and Institute of Biomaterials and Biomedical Engineering, University of Toronto, Canada; "Ventriculoperitoneal Shunt Flow Dependency on the Number of Patent Holes in a Ventricular Catheter," Pediatr Neurosurg 2000; 33:7-11; Original Paper; Received: Mar. 20, 2000; Accepted: Jun. 5, 2000.

\* cited by examiner

Prior Art

The following table assumes a catheter with an internal diameter of 1.2 mm and, therefore, an internal area of 1.131 mm².

| Hole Number | Inflow Position | Area Ratio | Total Hole Area [mm²] | Hole Dia [mm] |
|---|---|---|---|---|
| 1 & 2 | 9 | 0.0868 | 0.0982 | 0.2499 |
| 3 & 4 | 10 | 0.1077 | 0.1218 | 0.2784 |
| 5 & 6 | 11 | 0.1336 | 0.1511 | 0.3102 |
| 7 & 8 | 12 | 0.1658 | 0.1876 | 0.3456 |
| 9 & 10 | 13 | 0.2058 | 0.2328 | 0.3850 |
| 11 & 12 | 14 | 0.2555 | 0.2889 | 0.4289 |
| 13 & 14 | 15 | 0.3171 | 0.3586 | 0.4778 |
| 15 & 16 | 16 | 0.3935 | 0.4450 | 0.5323 |

METHOD OF DRAINING CEREBROSPINAL FLUID

REFERENCE TO RELATED APPLICATIONS

This application is a continuation-in-part of U.S. application Ser. No. 11/546,886, filed Oct. 12, 2006, which is divisional of U.S. application Ser. No. 10/400,363, filed Mar. 26, 2003, which claims priority from U.S. Provisional Application No. 60/367,565 filed on Mar. 26, 2002, the contents of each of which are incorporated in their entirety herein.

FIELD OF THE INVENTION

The invention relates generally to catheters. More particularly, the invention relates to a method of draining cerebrospinal fluid.

BACKGROUND OF THE INVENTION

Cerebrospinal fluid ("CSF") serves several important roles in the human body. The CSF provides buoyancy to the brain, which allows the brain to maintain its density without being impaired by its own weight. Without CSF, the weight of the brain would cut off blood supply in the lower sections of the brain, which could result in the death of neurons in these areas.

CSF protects the brain tissue from injury when jolted or hit. CSF thereby reduces the potential of hemorrhaging, brain damage or death caused by the brain being forced into contact with the skull.

CSF flows throughout the inner ventricular system in the brain and is absorbed back into the bloodstream, rinsing the metabolic waste from the central nervous system through the blood-brain barrier. This process allows for homeostatic regulation of the distribution of neuroendocrine factors, to which slight changes can cause problems or damage to the nervous system.

CSF is produced in the brain at a rate of between about 20 ml/hr and about 30 ml/hr. In a normal human, the CSF is absorbed into the body at a rate that is approximately the same as the rate at which the CSF is generated. This configuration enables the intracranial pressure to remain substantially consistent.

The human cranial compartment is incompressible which causes the volume inside of the cranium to be fixed. Within the cranium are located brain tissue, CSF and blood. These components are in a state of volume equilibrium such that any increase in the volume of one of these components must be compensated by a decrease in the volume of one of the other components.

A principal buffer within the cranium is CSF, the volume of which responds to increases or decreases of the other components within the cranium. Through such a change, it is possible to maintain the intracranial pressure within a normal range. Such a process is typically only effective for changes of volume of less than about 120 ml.

When in a laying down position, the typical intracranial pressure for adults is between about 7 and 15 mmHg. If the intracranial pressure exceeds 25 mmHg, a person may experience headache, vomiting, loss of consciousness, blindness and even death. Treatment is thereby warranted to reduce the intracranial pressure.

One technique that may be used to reduce the intracranial pressure is to provide more space for the brain tissue, CSF and blood by removing a portion of the person's cranium. Because of the potential risks of not having a complete cranium, this technique is generally reserved for only those situations where there are no other alternatives to maintain the intracranial pressure within the desired range.

While the increased intracranial pressure is far more common, it is also necessary to ensure that the intracranial pressure does not drop too low. The symptoms for intracranial hypotension are often similar to the symptoms of intracranial hypertension. As such, many medical experts believe that the symptoms are caused by the change in intracranial pressure as opposed to the pressure itself.

Based upon the preceding comments, it can be appreciated that it is important to prevent the amount of CSF from becoming too large or too low. For example, hydrocephalus is a medical condition that occurs when CSF builds up in the ventricles of the human brain. This build-up causes an abnormal and dangerous increase in intracranial pressure.

The typical procedure for treating hydrocephalus is to insert a drainage catheter into the ventricles of the brains. The drainage catheter enables the excess CSF to be diverted to another region of the human body where the CSF may be absorbed.

Catheters inserted for such a purpose are termed "proximal catheters." Some proximal catheters have one inlet hole by which CSF enters. Others have inlet holes along their longitudinal axis that vary in number, shape, distribution, and entrance conditions. The drainage section of these catheters is termed the "proximal end" and the end opposite the drainage section is the "distal end."

The flow rate of the CSF to be drained may be quite low. As a result, the CSF inflow into the various inlet holes of catheters used to treat these conditions is also quite low. It is commonly thought that only 1 or 2 inlet holes are required to permit adequate flow through proximal catheters and that most inlet holes are redundant.

A problem associated with CSF drainage catheters is tissue in-growth into the catheter holes. One potential factor believed to cause the tissue in-growth is the flow of CSF, which draws the choroid plexus tissue into the holes in the catheter.

It has been widely published that proximal catheters have a 30-40% chance of requiring emergency repair in the first year, and an 80% chance of failure after twelve years of implantation. The primary cause of the mechanical failures for these catheters is blockage of the most proximal inlet holes. Blockage is typically caused by CSF debris such as blood clots, cell clusters, brain parenchyma, and choroid plexus and ependymal tissue.

A study of proximal catheters was performed using the analytical tool of computational fluid dynamics ("CFD"). The purpose of the study was to determine the dynamics of inflow into the inlet holes of those catheters. The results of the study demonstrated that about 70% of the inflow into catheters having inlet holes of equal area occurred in the most proximal inlet holes.

Figure 5:
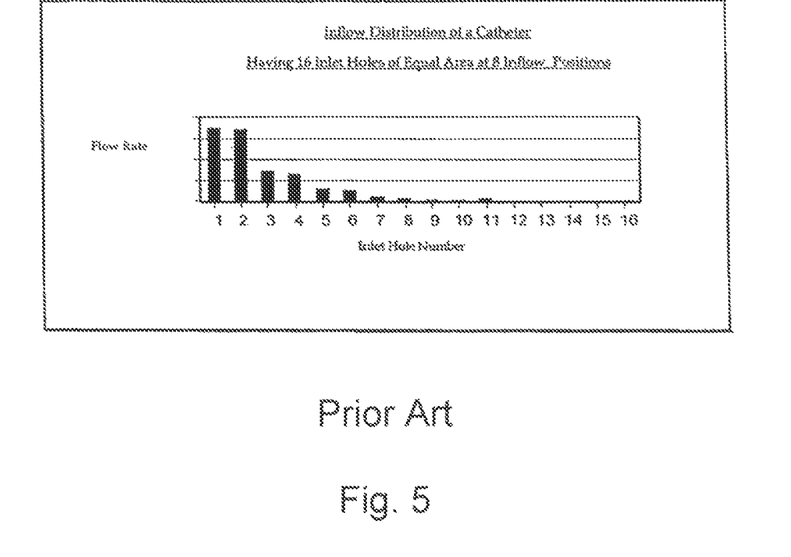
FIG. 5 graphically illustrates the fluid inflow distribution of a catheter having two inlet holes at eight inflow positions wherein all inlet holes have the same cross-sectional area.
Figure 6:
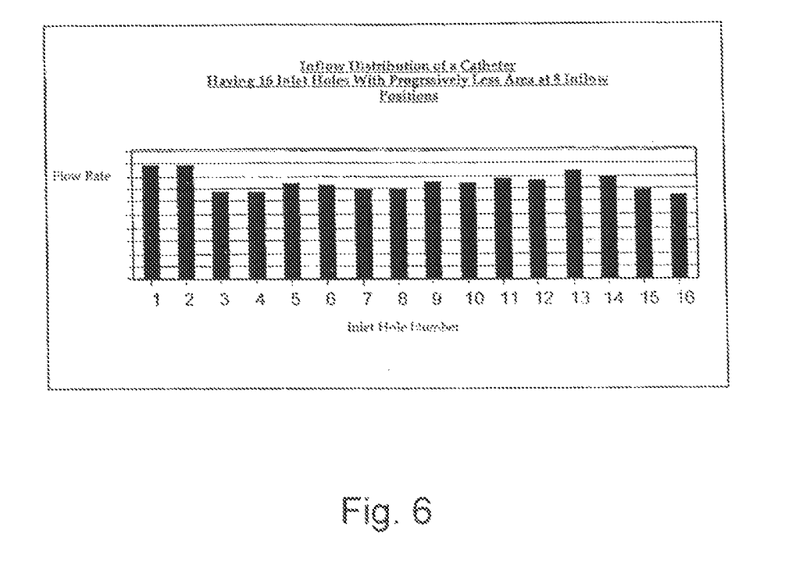
FIG. 6 graphically illustrates the fluid inflow distribution of one embodiment of the present invention having two inlet holes at eight inflow positions wherein the progressive decrease in the cross-sectional areas of the inlet holes was calculated using the curve illustrated in FIG. 7.

FIG. 5 shows the inflow distribution into a typical proximal catheter having sixteen inlet holes of equal cross-sectional area at eight inflow positions. An "inflow position" occurs at any position along the longitudinal axis of the catheter where at least one inlet hole is located. Inlet hole numbers 1 and 2 illustrated in FIG. 5 are located at the most proximal inflow position, i.e., the drainage end of the catheter.

As illustrated in FIG. 5, at low inflow rates fluid inflow into the various inlet holes of drainage catheters is not uniform. This disproportionate inflow causes a disproportionate amount of debris to be deposited within these inlet holes as well as in the catheter passageway at the location of these inlet holes. Because these most proximal inlet holes are located at the drainage end of the catheter, blockage at this point results in drainage failure for the entire catheter.

Numerous designs have been attempted to guard against debris being deposited onto and into drainage catheters. Some attempts have been made to add physical guards to the external surface of drainage catheters.

Other attempts have focused on the valves that are used to regulate the fluid flow out of the catheters. The present invention, however, focuses on the catheter inlet holes themselves and the fluid dynamics that underlie the mechanics behind fluid entry into those inlet holes.

Wolter, U.S. Pat. No. 5,451,215, discloses a suction drain that is described as being intended for use with removing discharges from wounds. The Wolter catheter includes a tubular structure with a distal end and a proximal end.

A cap containing antibacterial material is attached to the distal end to substantially seal the distal end. The cap allows the antibacterial material to be discharged into the region surrounding the distal end to minimize the potential of an infection developing in such region.

Proximate the distal end, a plurality of openings are formed in the tubular structure. The diameter of the openings decreases in the direction of suction. This configuration provides a suction effect that is approximately the same in the region of such openings.

The proximal end is attached to a source of reduced pressure such as a vacuum source. This reduced pressure causes discharge proximate the distal end to be drawn through the openings, into the tubular structure and then towards the proximal end. This negative pressure is typically on the order of several inches of $H_2O$.

Wolter indicates that this configuration causes the antibacterial material to move lengthy distances through the body tissue until the antibacterial material is removed by suction through the openings that extend along opposite sides of the tube.

In wound drainage, it is desired to draw debris present in the wound into the catheter. Through such a process, the debris is removed from the wound, which enhances the rate at which the wound heals.

SUMMARY OF THE INVENTION

An embodiment of the invention is directed to a method of draining cerebrospinal fluid from a human brain. A drainage catheter is provided having a proximal end and a distal end. The drainage catheter has a plurality of openings formed therein. The plurality of openings includes a first opening, a second opening, and a most proximal opening. The second opening is disposed closer to the distal end than the first opening. A cross-sectional area of the first opening is less than a cross-sectional area of the second opening.

The distal end of the drainage catheter is inserted into a human brain. Cerebrospinal fluid is drained from the human brain. The cerebrospinal fluid passes into the drainage catheter through the plurality of openings and out of the drainage catheter through the proximal end. A rate at which the cerebrospinal fluid passes through the drainage catheter is controlled to maintain intracranial pressure within a selected range.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE PREFERRED EMBODIMENTS

An embodiment of the invention is directed to a method of removing cerebrospinal fluid using a catheter that is implanted in one of the ventricles of a human brain. The method thereby enables intracranial pressure to be maintained within a desired range of between about 15 and 25 mm Hg.

Drainage catheters can be improved by designs that force the fluid to be drained into a greater number of inlet holes. The present invention accomplishes this by progressively decreasing the cross-sectional areas of the inlet holes as the proximal end of the catheter is approached.

FIGS. 1-4 show a catheter 1 as an elongated tube in accordance with an embodiment of the invention. The catheter 1 has a proximal end 2 and a distal end 3. The distal end 3 is adapted for implantation into a body cavity of an animal and the proximal end 2 is adapted for connection to means to divert fluid from that particular body cavity.

The catheter 1 has an annular wall 4 that defines a central passageway 5. Along the longitudinal axis of the wall 4 two or more inflow positions 6, 7, 8 can be identified. At each inflow position 6, 7, 8 there are one or more inlet holes 9, 10, 11, 12, 13. The inlet holes 9, 11, 13 at each inflow position 6, 7, 8 progressively decrease in cross-sectional area as the inflow positions 6, 7, 8 approach the proximal end 2 of the catheter 1.

The catheter 1 so designed may be used to divert fluid from any body cavity where the fluid flow dynamics can be described in the art as "laminar flow" and, more specifically, by mathematically expressing the flow as a Reynolds number between 20 and 800. It is not a limitation of this invention that the inflow positions 6, 7, 8 be equidistant.

Figure 1:
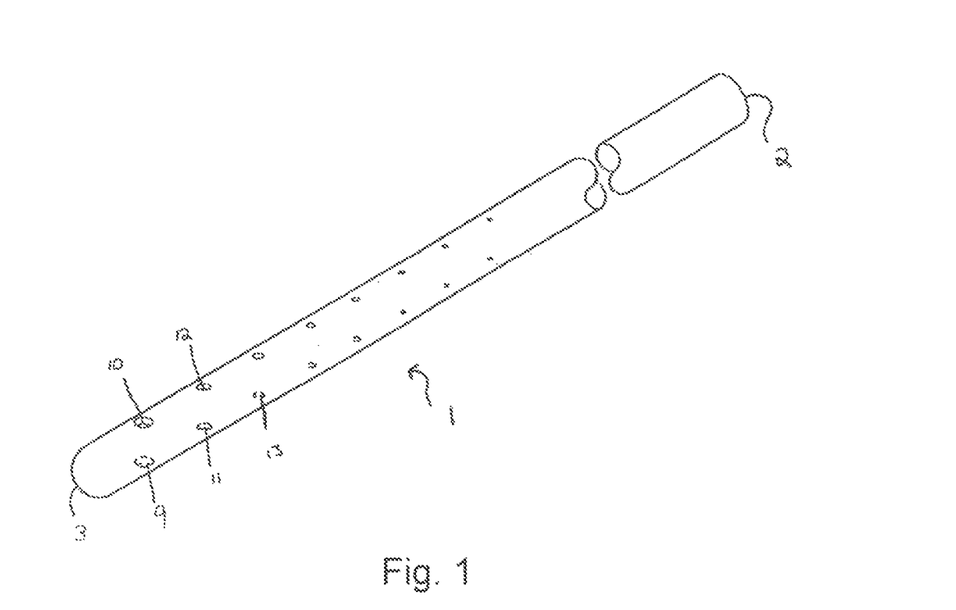
FIG. 1 illustrates an embodiment of the present invention having two inlet holes at eight inflow positions.
Figure 2:
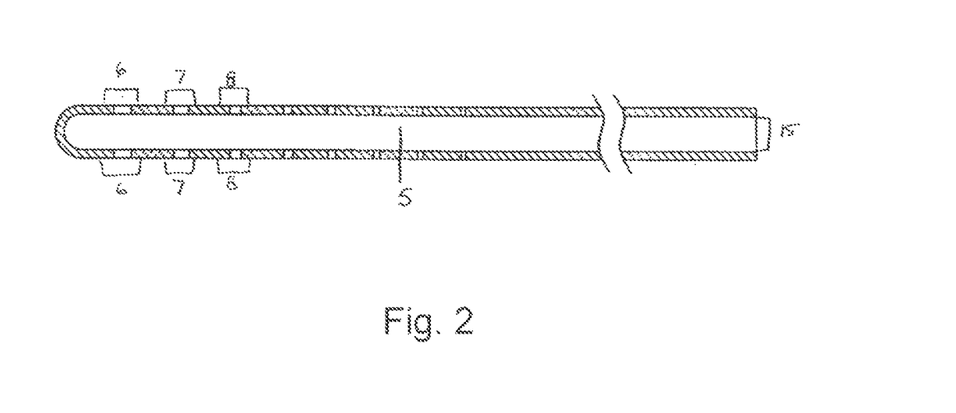
FIG. 2 is a cross-sectional view of FIG. 1.

The space located at the distal end 14 of the catheter 1 functions to maintain the structural integrity of the catheter and may have any length that provides that integrity in order to accomplish the purpose for which the particular catheter is used. It is understood that the overall dimensions of the present invention can vary.

Figure 3:
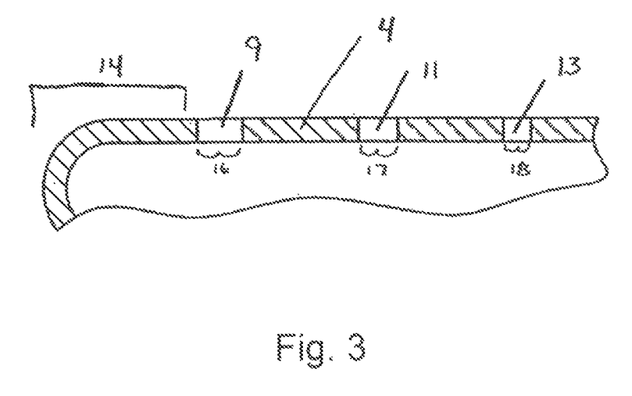
FIG. 3 illustrates a portion of another embodiment of the present invention having one inlet hole at three inflow positions.

FIG. 3 illustrates one embodiment of the invention. One inlet hole is located at each of three inflow positions along the longitudinal axis of the catheter 1. Each inlet hole 9, 11, 13 has a smaller cross-sectional area 16, 17, 18 than the one preceding it.

Figure 4:
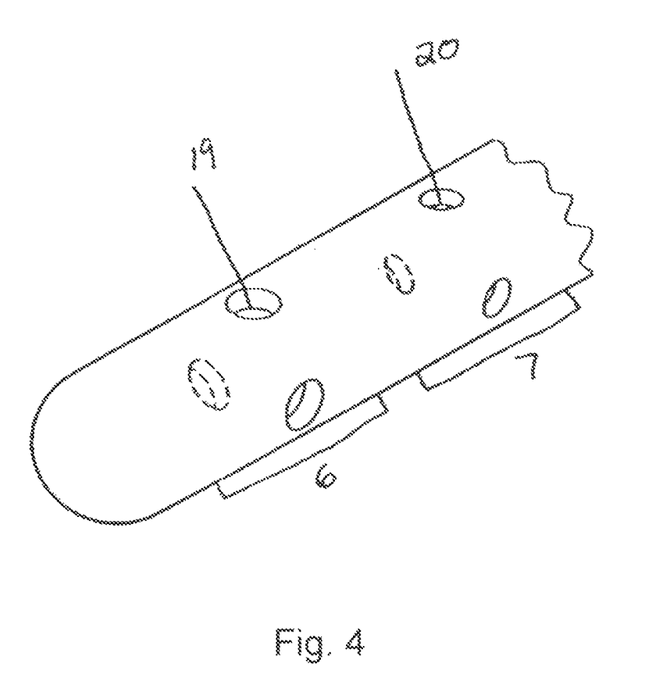
FIG. 4 illustrates a portion of a further embodiment of the present invention having three inlet holes at two inflow positions.

FIG. 4 illustrates another embodiment of the invention. Three round inlet holes are located at each inflow position 6 and 7. The cross-sectional area of each inlet hole at inflow position 7 is less than the cross-sectional area of each inlet hole at inflow position 6.

In an exemplary embodiment, the catheter 1 can be used to divert CSF from the ventricles of a human brain. In this embodiment, the catheter 1 has a length that ranges from about 10 centimeters to about 50 centimeters. The inner diameter 15 of the catheter ranges from about 1.0 millimeters to about 3.0 millimeters.

The progressive decrease in the inlet holes 9, 11, 13 cross-sectional areas 16, 17, 18 need not be uniform. However, a method is herein described that results in near equal fluid inflow into the inlet holes 9, 10, 11, 12, 13 at each inflow position 6, 7, 8.

The primary variable that controls fluid inflow into a proximal catheter is the distribution of the total hole areas along its longitudinal axis. "Total hole area" is defined as the sum of all the inlet hole areas at a given inflow position 9, 10. "Inlet hole area" is defined as, and is used interchangeably with, the cross-sectional area of one inlet hole.

The phrase "distribution of the total hole areas" is understood to mean the pattern of change in the total hole areas along the longitudinal axis of the catheter 1. Through the tools of computational fluid dynamics and experiment, the distribution of the total hole areas was calculated and optimized to approximate equal inflow into each inflow position for a number of catheter operating conditions, typical implant positions, and body locations.

This optimization was accomplished by numerically solving the conservation equations involving mass, energy, and momentum that govern the flow fields to and within the subject catheters. Total hole areas were adjusted for each computational trial until approximately equal inflows were obtained at each inflow position for every catheter analyzed in the study.

Figure 7:
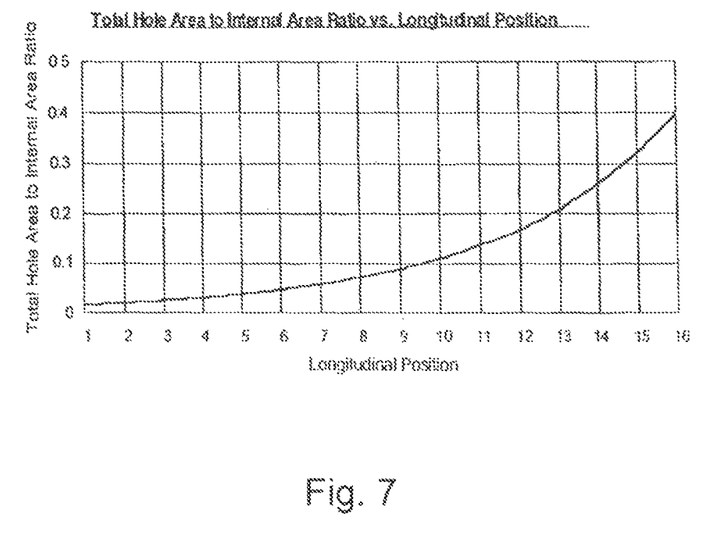
FIG. 7 illustrates the curve that can be used to design one embodiment of the present invention whereby the fluid inflow distribution is essentially uniform at all inflow positions.

FIG. 7 displays a total hole area distribution curve that provides the means for producing approximately equal inflows in proximal catheters having four to sixteen inflow positions. This distribution curve was generated by compiling all the calculations from the CFD analysis and is, therefore, a generalized curve that can be applied to the manufacture of proximal catheters irrespective of any particular proximal catheter's dimensions.

The curve was plotted as the ratio between the total hole area at each inflow position and the internal diameter 15 of a proximal catheter having an internal diameter 15 of 1.2 millimeters. The curve can be expressed mathematically by the equation $F(X)=0.0699*\exp[0.216*(X-8)]$ where $F(X)$ is the y-coordinate of the graph at FIG. 7, X is the x-coordinate of the graph at FIG. 7, and exp is the exponent "e" (approximately 2.71828).

Figure 8:
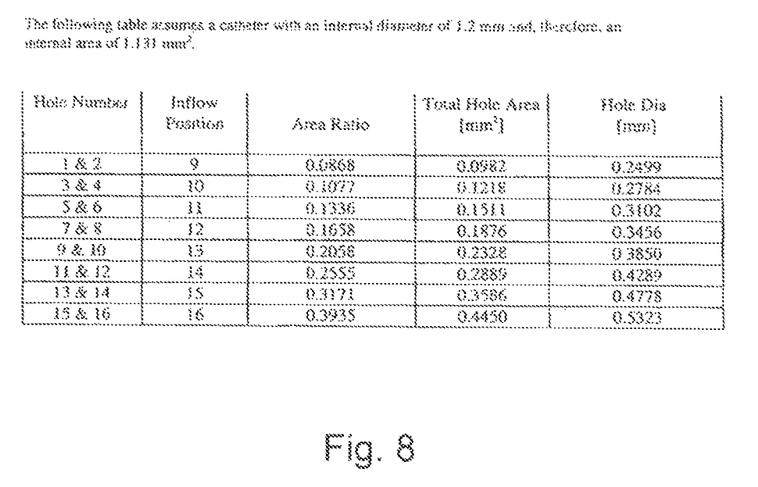
FIG. 8 provides in tabular form the measurements illustrated by the curve in FIG. 7.

The sixteenth inflow position of the curve is located at the most distal end of the catheter, i.e., the end furthest from the draining end of the catheter. The curve has been normalized for a sixteen inflow position catheter. FIG. 8 provides in tabular form the measurements illustrated by the curve in FIG. 7.

To design a proximal catheter by utilizing the curve, a catheter designer must first define the catheter's inner diameter 15. The inner diameter 15 of many proximal catheters is 1.2 millimeters. After selecting an inner diameter, a catheter designer intent on making a twelve inflow position catheter, for example, would merely apply the value at curve inflow position sixteen to calculate the total hole area for his or her twelfth inflow position.

The designer would then apply the value at curve inflow position fifteen to calculate the total hole area at his or her eleventh inflow position. In like manner, the designer can calculate the remaining total hole areas. The designer would then select the number of inlet holes 9, 10, 11, 12, 13 desired at each inflow position 6, 7, 8 and divide each calculated total hole area by that number.

Because the curve defines the total hole area at the various inflow positions, any number of inlet holes at any one inflow position may be selected. The result of this calculation for each inflow position will be the inlet hole area 16, 17, 18 for each inlet hole at each inflow position. For example, a catheter as represented by FIG. 8 has an internal diameter of 1.2 mm.

The catheter includes sixteen holes divided into eight pairs, one for each of the eight inflow positions: 9-16. In this example, hole diameters for each hole of the pair at that inflow positions ordered from the most distal inflow position, inflow position 16, to the most proximate inflow position, inflow position 9, are as follows: 0.5323 mm, 0.4778 mm, 0.4289 mm, 0.3850 mm. 0.3456 mm, 0.3102 mm, 0.2784 mm and 0.2499 mm.

The present invention is intended to include all variations in the distribution of total hole areas along the longitudinal axis so long as the inlet holes 9, 11, 13 at each inflow position 6, 7, 8 progressively decrease in cross-sectional area as the inflow positions 6, 7, 8 approach the proximal end 2 of the catheter 1. The means in the exemplary embodiment for making this progressively decreasing distribution of total hole areas is but one embodiment of the present invention.

By dividing the CSF flow more evenly among all of the flow holes through the progressively larger hole sizes, the magnitude of the flow at any one point is greatly reduced. Through such a process, there is less force available to drag the choroid plexus tissue into the holes to thereby delay or prevent occlusion of the catheter.

The invention is not limited by any particular shape or shapes of the inlet holes 9, 10, 11, 12, 13. It is also intended that all changes in the total hole areas resulting from altered entrance conditions of the inlet holes, such as an angled entrance or slits in the wall 4 of the catheter 1 adjacent to and in communion with the inlet hole, are within the scope of this invention.

Figure 9:
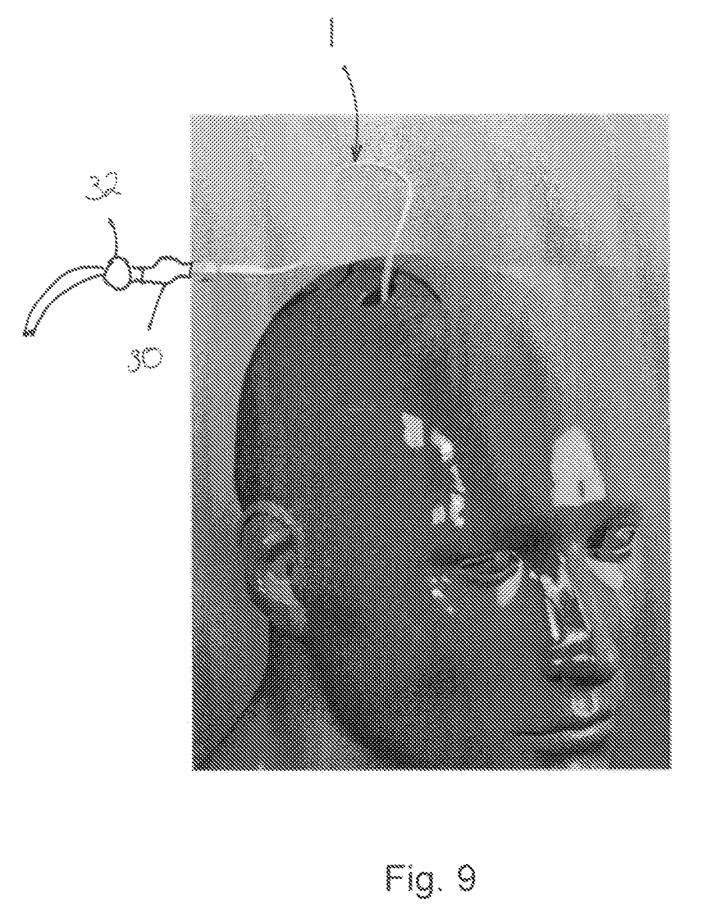
FIG. 9 is an illustration of a cerebrospinal fluid removal system according to an embodiment of the invention.

In addition the catheter 1 discussed above, the invention is also directed to a system as illustrated in FIG. 9 for removing CSF from around a human brain. The CSF removal system may also include a pressure monitoring device 30. In certain embodiments, the pressure monitoring device 30 is a pressure transducer.

The pressure transducer may be operably connected to the catheter 1. Such a configuration enables the intracranial pressure to be monitored while the excess CSF is being removed from inside of the cranium. Alternatively or additionally, the pressure transducer may be separately attached to the person's head.

The CSF removal system may also include a valve 32 that is operably attached to the catheter. The valve 32 may be used to control the rate at which the cerebrospinal fluid is removed from the cranium to thereby maintain the intracranial pressure within a desired range.

It is also possible for the pressure monitoring device 30 and the valve 32 to linked or otherwise connected such that the position of the valve 32 may be changed in response to the intracranial pressure that is monitored by the pressure monitoring device 30.

It is also possible for the CSF removal system to include a collection vessel that is operably attached to the catheter. The collection vessel receives CSF that is removed from the cranium. Alternatively, the CSF removed from inside of the cranium may be directed to another location within the person's body where it is possible for the CSF to be absorbed into the tissue.

The drawings are understood to be illustrative of the concepts disclosed herein to facilitate an understanding of the invention. Further, the drawings are not to scale, and the scope of the invention is not to be limited to the particular embodiments shown and described herein.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the FIGURE(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A method of draining cerebrospinal fluid from a human brain, the method comprising:
providing a drainage catheter having a proximal end and a distal end, wherein the drainage catheter has a plurality of openings formed therein, wherein the plurality of openings includes a first opening, a second opening, and a most proximal opening, wherein the second opening is disposed closer to the distal end than the first opening and wherein a cross-sectional area of the first opening is less than a cross-sectional area of the second opening;
inserting the distal end of the drainage catheter into a human brain;
diverting excess cerebrospinal fluid from the human brain, wherein the cerebrospinal fluid passes into the drainage catheter through the plurality of openings and out of the drainage catheter through the proximal end; and
distributing the draining of the cerebrospinal fluid between the plurality of openings, wherein the distributed flow of cerebrospinal fluid delays or prevents occlusion of the catheter caused by choroid plexus tissue being drawn into the plurality of openings.

2. The method of claim 1, and further comprising accumulating over time a greater amount of debris deposits in the second opening as compared to the most proximal opening.

3. The method of claim 1, further comprising connecting the proximal end of the catheter to a component to divert the cerebrospinal fluid received by the plurality of openings from the human brain.

4. The method of claim 1, wherein a ratio of total hole area to an internal area of the drainage catheter is $0.0699*\exp[0.216*(X-8)]$ where X is a longitudinal position along the drainage catheter.

5. The method of claim 1, wherein the plurality of openings are formed at a plurality of inflow positions with at least one opening being formed at each of the inflow positions, wherein each inflow position has a total hole area, wherein the inflow positions include a first inflow position and a second inflow position, the second inflow position being disposed closer to the distal end than the first inflow position, and wherein the total hole area at the first inflow position is less than the total hole area at the second inflow position.

6. The method of claim 5, wherein the total hole area at the plurality of inflow positions increases with distance of the inflow positions from the proximal end.

7. The method of claim 5, wherein the total hole area at the first inflow position is approximately 0.1 square millimeters and the total hole area at the second inflow position is approximately 0.2 square millimeters.

8. The method of claim 1, wherein the drainage catheter has an inner passageway with a uniform inner diameter, wherein the uniform inner diameter is between approximately 1.0 millimeter and approximately 3.0 millimeters.

9. The method of claim 8, wherein the uniform inner diameter is approximately 1.2 millimeters.

10. The method of claim 1, wherein the second opening has a diameter of approximately 0.5 millimeters.

11. The method of claim 1, wherein draining fluid includes allowing substantially equal fluid flow into each of the plurality of openings.

12. The method of claim 1, wherein the cross-sectional areas of the plurality of openings increase with distance from the proximal end.

13. The method of claim 1, wherein inserting the drainage catheter into the human brain comprises inserting the drainage catheter into a ventricle of the human brain.

14. The method of claim 1, wherein the human brain is part of a patient with hydrocephalus.

* * * * *